United States Patent [19]

Alfatafta et al.

[11] Patent Number: 5,672,621

[45] Date of Patent: Sep. 30, 1997

[54] CARBONARIN ANTIINSECTAN METABOLITES

[75] Inventors: Ali A. Alfatafta, Amman, Jordan; Patrick F. Dowd, Peoria, Ill.; James B. Gloer, Iowa City, Iowa; Donald T. Wicklow, Peoria, Ill.

[73] Assignees: The United States of America as represented by the Secretary of Agriculture, Washington, D.C.; University of Iowa Research Foundation and Biotechnology Research and Development Corp., Peoria, Ill.

[21] Appl. No.: 608,170

[22] Filed: Feb. 27, 1996

Related U.S. Application Data

[63] Continuation-in-part of Ser. No. 283,034, Jul. 29, 1994, Pat. No. 5,519,052.

[51] Int. Cl.[6] .................. A10N 43/16; A61K 31/40; C07D 207/46; C07D 311/80
[52] U.S. Cl. .................. 514/422; 514/423; 514/455; 548/525; 548/530; 549/393; 549/395
[58] Field of Search .................. 514/422, 423, 514/455; 548/525, 530; 549/393, 395

[56] References Cited

U.S. PATENT DOCUMENTS

| | | | |
|---|---|---|---|
| 5,017,598 | 5/1991 | Dowd et al. | 514/415 |
| 5,519,052 | 5/1996 | Alfatafta et al. | 514/455 |

OTHER PUBLICATIONS

Gloer, et al, *J. Org. Chem.*, (1988). 53, pp. 5457–5460.
Gloer, et al, *J. Org. Chem.*, (1989). 54, pp. 2530–2532.
Gorst–Allman, *J. Chem. Soc. Perkin Trans. 1*, (1980). pp. 2474–2479.
Priestap, *Tetrahedron*, (1984). 40, pp. 3617–3624.
Priestap, *Magn. Reson. Chem.*, (1986). 24, pp. 875–878.
Turner, *Fungal Metabolites II*, Academic Press: New York, (1983). p. 21.
Wicklow, et al, *Can J. Bot.*, (1982). 60, pp. 525–528.
Wicklow, et al, *Trans. Br. Mycol Soc.*, (1988). 91, pp. 43–438.
Gloer, et al, *J. Org. Chem.*, (1990). 55, pp. 5299–5301.

*Primary Examiner*—Johann Richter
*Assistant Examiner*—Jane C. Oswecki
*Attorney, Agent, or Firm*—Arnold, White & Durkee

[57] ABSTRACT

Carbonarins A, B, C, D, E, F, G, and H have been isolated from the sclerotia of the fungus *Aspergillus carbonarius*. The carbonarius are effective for controlling Coleopteran and Lepidopteran insects. The carbonarins have the structure:

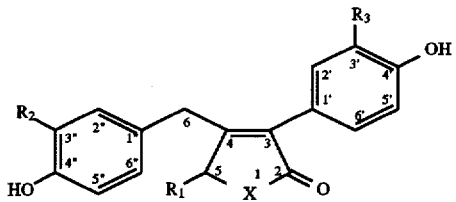

wherein: $R_1$ is a hydrogen atom or a hydroxy group; $R_2$ is a hydrogen atom or a methoxy group; $R_3$ is a hydrogen atom or a naphthopyrone group; and X is an oxygen atom or an NH group.

27 Claims, No Drawings

CARBONARIN ANTIINSECTAN METABOLITES

CROSS REFERENCE TO RELATED APPLICATION

This application is a continuation-in-part application of U.S. application Ser. No. 08/283,034 filed Jul. 29, 1994, U.S. Pat. No. 5,519,052.

FIELD OF THE INVENTION

The present invention is generally related to carbonarin compounds. More specifically, the carbonarin compounds are used as insecticides, e.g., for control of Lepidoptera or Coleoptera species.

BACKGROUND OF THE INVENTION

Certain fungi produce specialized resting bodies known as sclerotia as a means for surviving adverse environmental conditions which other fungal bodies cannot tolerate, such as harsh climate, nutrient deficiency and desiccation. Generally, sclerotia remain viable in soil for periods of several years, and provide primary inoculum for the producing species when conditions again become favorable for fungal growth. Sclerotia are formed under natural conditions or in solid substrate fermentations, but are not commonly produced in the liquid fermentation cultures generally employed in studies of microbial metabolites. Accordingly, many novel sclerotial metabolites of common fungi such as Aspergillus have not been characterized.

While sclerotia are known to contain biologically active secondary metabolites not found in other fungal parts or in liquid cultures, study of sclerotia as sources of novel metabolites has been limited. Investigation of large sclerotia (ergots) of *Claviceps purpurea* led to the discovery and medicinal use of ergot alkaloids.

Sclerotia have recently been recognized as a valuable potential source for natural antiinsectans. Many sclerotia, which are subjected to predation by fungivorous insects and arthropods during their period of dormancy in soil, have been shown to contain metabolites that exert adverse physiological effects on insects. [Gloer et. al, 1988 and Wicklow et. al, 1988] disclose the isolation of four antiinsectan aflavanine derivatives from the sclerotia of *Aspergillus flavus* for use in controlling the dried-fruit beetle *Carpophilus hemipterus* (Nitidulidae:Coleoptera). [TePaske et. al, 1990] disclose a related metabolite, aflavazole, which was isolated from extracts of *A. flavus sclerotia*. [Gloer et. al, 1989] describe an insecticidal indole diterpene known as nominine found only in the sclerotia of *Aspergillus nomius* for the control of the corn earworm *Helicoperva zea* (Lepidoptera), formerly *Heliothis zea*. Nominine is also disclosed by Dowd et al. in U.S. Pat. No. 5,017,598 issued May 21, 1991,and entitled "Nominine, an Insecticidal Fungal Metabolite".

There remains a continuing need for new insecticides because many agriculturally important insect species have developed a resistance to the most potent insecticides which are currently available. Moreover, the number of available environmentally tolerable replacements for these insecticides is declining. New natural, biodegradable insecticides which are relatively nontoxic to vertebrates and may be produced by fermentation processes are a cost effective replacement for known insecticides.

SUMMARY OF THE INVENTION

In order to satisfy the need for a cost effective, natural, biodegradable insecticide, one aspect of the present invention provides substantially pure carbonarin compounds which are effective for controlling Lepidopteran or Coleopteran insects. The carbonarins have the structure:

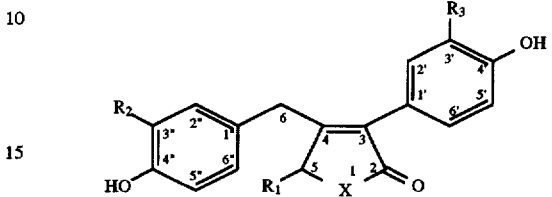

wherein: $R_1$ is a hydrogen atom or a hydroxy group; $R_2$ is a hydrogen atom or a methoxy group; $R_3$ is a hydrogen atom or a naphthopyrone group; and X is an oxygen atom or an NH group.

In preferred embodiments, the carbonarins of the present invention have the following preferred structures:

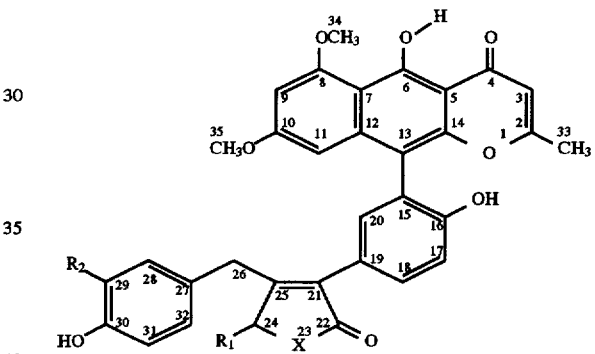

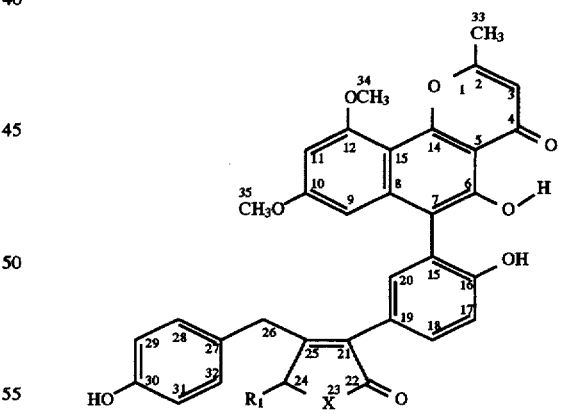

Carbonarin A: X = O   $R_1$ = OH   $R_2$ = H
Carbonarin B: X = O   R = OH
Carbonarin C: X = NH  $R_1$ = H    $R_2$ = H
Carbonarin D: X = NH  R = H
Carbonarin F: X = O   $R_1$ = OH   $R_2$ = OCH$_3$
Carbonarin G: X = O   $R_1$ = H    $R_2$ = OCH$_3$
Carbonarin H: X = O   $R_1$ = H    $R_2$ = H

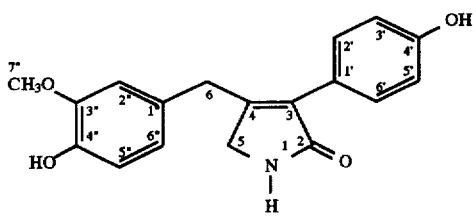

Carbonarin E

Another aspect of the present invention provides a composition for controlling insects containing carbonarins A, B, C, D, E, F, G and/or H and an inert carrier. The compound is preferably present in the composition in an amount sufficient to control insects of the Lepidopteran or Coleopteran species such as *Helicoverpa zea, Carpophilus hemipterus* or *Spodoptera frugiperda*. An effective amount of the composition may be applied to a locus of insects in order to control the insects.

DETAILED DESCRIPTION OF THE INVENTION

The present invention provides several substantially pure carbonarin compounds effective in controlling insects, insecticidal compositions containing a compound of the present invention and a method for controlling insects by applying the compositions to the locus of the insects. The compounds of the present invention have the structure:

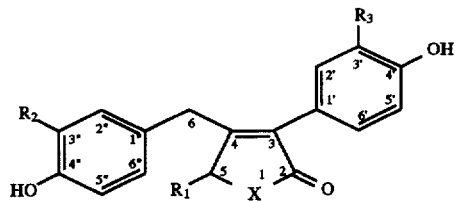

wherein $R_1$ is a hydrogen atom or a hydroxy group; $R_2$ is a hydrogen atom or a methoxy group; $R_3$ is a hydrogen atom or a naphthopyrone group; and X is an oxygen atom or an NH group.

Examples of naphthopyrone groups are:

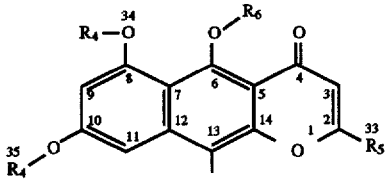

and

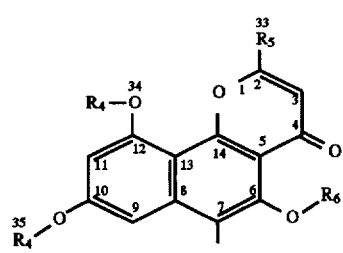

wherein $R_4$ and $R_5$ are individually hydrogen or alkyl groups such as methyl, ethyl, propyl, and butyl; and $R_6$ is —H or —C(=O)$R_7$ where is hydrogen or an alkyl group such as methyl, ethyl, propyl, and butyl.

Preferred carbonarins include carbonarins A, B, C, D, E, F, G, and H, and have the structures:

Carbonarin A:

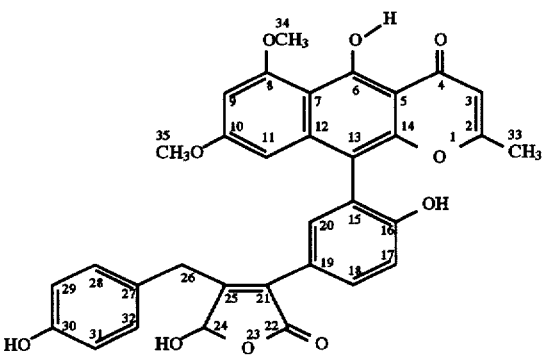

Carbonarin B:

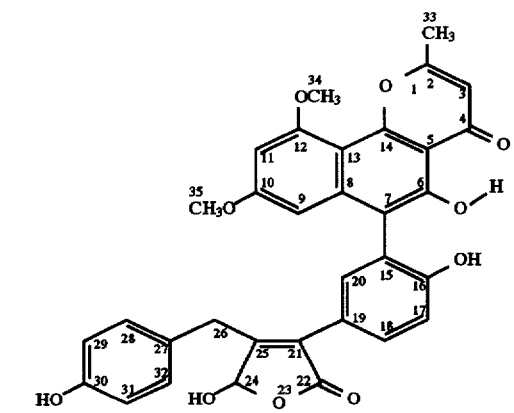

Carbonarin C:

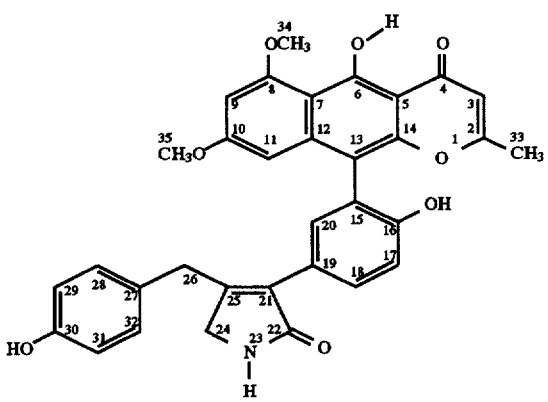

Carbonarin D:

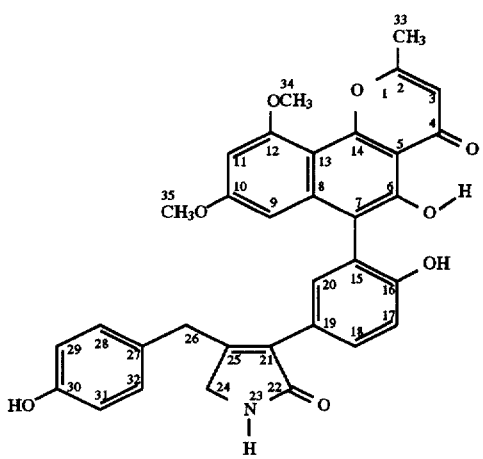

Carbonarin E:

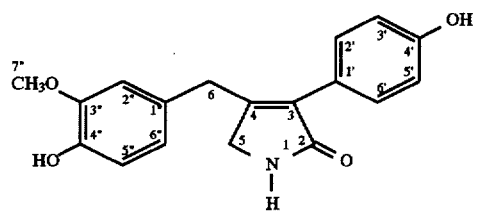

Carbonarin F:

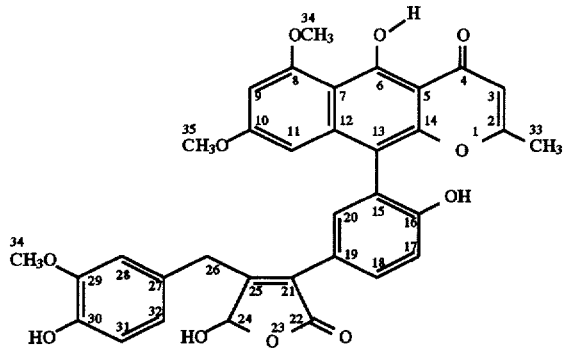

Carbonarin G:

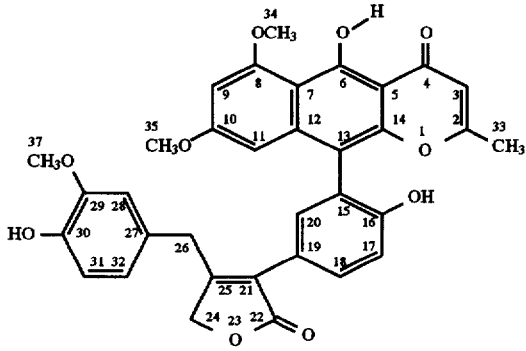

and Carbonarin H:

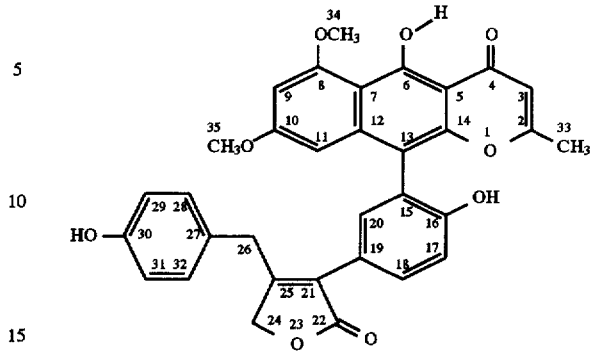

Carbonarin A, B, C, D, E, F, G, and H are isolated from file sclerotia of the fungus *Aspergillus carbonarius* (NRRL 369). Sclerotia are specially adapted multicellular structures produced by many fungi as a mechanism for propagation and survival [Gloer et. al, 1988; Gloer et. al 1989; Wicklow et. al, 1982; Wicklow et. al, 1988]. The sclerotia of *A. carbonarius* are produced by solid-substrite fermentation on corn kernels and ground by conventional means to a suitable particle size and are extracted with at least one solvent. Suitable solvents for the extraction are well known to a skilled artisan and would include any solvents in which the compounds of the present invention are soluble. Preferably, the ground sclerotia of *A. carbonarius* are sequentially extracted with methanol (MeOH), $CHCl_3$, and aqueous methanol (10% $H_2O$). The methanol extract of *A. Carbonarius* sclerotia showed antiinsectan activity against the corn earworm *Helicoverpa zea* and the fungivorous beetle *Carpophilus hemipterus*.

Isolation and purification of the compounds of the present invention from the solvent extract is performed by the use of conventional techniques, such as high-performance liquid chromatography (HPLC), thin layer chromatography (TLC), silica gel column chromatography and/or countercurrent distribution (CCD). In a preferred embodiment of the invention, a solvent extract is separated by silica gel column chromatography, and the resulting fraction is further separated by HPLC. Carbonarins A, B, C, D, E, F, G, and H are isolated using this procedure as described in further detail in the examples herein, although the procedures are not limited thereto.

Commercial formulations including the compounds of the present invention may be prepared directly from fungal extracts or from the fractions derived from the extracts. However, the formulations are prepared from a pure or a substantially pure compound when a high degree of specificity is required. For example, if a high degree of predictability of the intended response by both target and nontarget species is required, a formulation prepared from a pure or substantially pure form of a compound of the present invention would be used. The formulation would then exclude other substances found in natural fungi which might have an adverse effect on activity or a toxic effect toward nontarget species.

Insecticidal compositions of the present invention include carbonarin A, B, C, D, E, F, G, and H as described herein in combination with a suitable inert carrier as known in the art. Agronomically acceptable carriers such as alcohols, ketones, esters and surfactants are illustrative. A compound of the present invention is present in the composition in an amount effecting the target species which is typically at least about 1.0 ppm and up to as much as 5% or more, preferably about 0.1% to about 5%. The concentration of the compound in an insecticidal composition will vary considerably depending upon the target species, substrate, method of application and desired response. Additional factors to be considered in determining an optimum concentration include phytotoxicity toward the treated plant and the tolerance of nontarget species.

The compounds of the present invention act to control pests by mechanisms including growth regulation, death inducement, sterilization, as well as interference with metamorphosis and other morphogenic functions. The resulting response is dependant on the pest species, the compound concentration and method of application. The compound is administered in an amount effecting one or more of the responses as may be predetermined by routine testing. Where the intended response is pest mortality, an "effective amount" is defined as the quantity of the compound which will effect a significant mortality rate of a test group as compared with an untreated group. Alternatively, where the intended response is a reduction in growth rate, reduction in feeding rate or reduction in damage, an effective amount is that amount sufficient to elicit the intended response. The actual effective amount will vary with the species of pest, stage of larval development, nature of the substrate, the type of inert carrier, the period of treatment and other related factors.

The compositions of the present invention are effective in controlling a variety of insects. Agronomically important insects such as those of the orders Lepidoptera and Coleoptera are of particular interest. However, the compounds and compositions of the present invention are not limited thereto.

The insecticidal compositions of the present invention are used to control insects by applying the composition to the locus of the pest to be controlled. When the compound is intended as a stomach poison, it is applied in conjunction with an inert carrier to the pest diet. The composition is applied to plants by treating the leaf surfaces or by systematic incorporation. As a contact poison, any topical method of application will be effective, such as direct spraying on the pest or on a substrate which is likely to be contacted by the pest.

The following examples are presented to describe preferred embodiments and utilities of the present invention and are not meant to limit the present invention unless otherwise stated in the claims appended hereto.

EXAMPLES

General Experimental Procedures

The strain of *A. carbonarius* NRRL 369 (=Thom No. 4030-1; =WB 369; =CBS 556.65) was obtained from the USDA Agricultural Research Culture Collection, National Center for Agricultural Utilization Research, Peoria, Ill. This strain was isolated from an unknown source by A. F. Blakeslee, Storrs, Conn. and sent to C. Thom, Bureau of Chemistry, Department of Agriculture, Washington, D.C. [Turner, 1983]. Because Bainier's type strain had been lost, [Al-Musallam, 1980]designated CBS 556.65, received as WB 369 from K. B. Raper in 1965, as neotype culture and specimen. The sclerotia were prepared using general procedures described elsewhere and incorporated herein by reference [Wicklow et. al, 1988]. The dried ground sclerotia were suspended in MeOH and stirred at room temperature for 12 h. This process was repeated four times (4×2 L). The combined organic extracts were evaporated under reduced pressure to yield a brown oily residue (6.6 g) which exhibited antiinsectan activity.

HRFAB and LRFAB mass spectra were recorded on a VG ZAB-HF mass spectrometer. UV spectra were recorded with a Beckman model 168 photodiode array detector, and optical rotations were determined in methanol using a Perkin-Elmer 141 polarimeter. Preparative HPLC separations were conducted using a Rainin Dynamax-60A axial compression column (21.4 mm, ×25 cm; 8 µm particle size) at a flow rate of 10 mL/min with UV monitoring at a wavelength of 215 nm. $^1$H NMR, $^{13}$C NMR, DEPT, and selective INEPT spectra (optimized for J=4 or 7 Hz) were recorded on a Broker AC-300 spectrometer unless otherwise specified. Solvent signals were used as internal references for the assignment of chemical shifts. Carbon multiplicities were established by DEFT experiments. HMBC (optimized for J=8 Hz), HMQC (optimized for J=152 Hz), and NOESY data were obtained using a Broker AMX-600 spectrometer. All NMR experiments were conducted in acetone-$d_6$ unless otherwise noted.

Example 1 Isolation of Carbonarins A, B, C, D, and E

The MeOH extract of the ground selerotia was partitioned between $H_2O$(1L) and $CHCl_3$ (4×1 L). The resulting organic extracts were combined, evaporated under reduced pressure, and redissolved in 10% $H_2O$/MeOH. This mixture was extracted with hexane (4×2 L) to remove nonpolar, inactive material. The aqueous MeOH fraction was evaporated under reduced pressure to afford a yellowish residue (1.14 g) which was fractionated on a Si gel flash column (100 g of $GF_{254}$; 60–200 mesh; Fluka) using increasing concentrations of MeOH in $CHCl_3$. This column afforded six fractions. Fraction 2 (86 mg) eluted with 7% MeOH—$CHCl_3$ (2×500 mL), and contained a complicated mixture of a highly aromatic compounds as indicated by its $^1$H NMR spectrum. This fraction was subjected to preparative HPLC using 60% MeOH/$H_2O$ to obtain carbonarins A(13.3 mg), B(6.4 mg), C(5.2 mg), D(0.7 mg), and E(6.7 mg).

Carbonarin A:

$t_R$ 19.0 min.; $[\alpha]_D$=0° (0.08 g/dL); $[\alpha]_{Hg}$=−15.6° (0.08 g/dL); UV (MeOH) 228 nm (ε=23900), 280 nm (ε=27000), 410 nm (ε=4200); IR ($CHCl^3$) 1759 cm$^{-1}$, 1652 cm$^{-1}$, 1613 cm$^{-1}$, LRFABMS (thioglycerol) ions at m/z 583 ([M+H]$^+$, 100), 488 (8), 471 (13), 451 (7), 446 (19), 429 (54), 413 (7), 371 (9), 363 (9); HRFABMS (glycerol), obsd, 583.1648 (M+H); calcd for $C_{33}H_{26}O_{10}$+H, 583.1604 (Δ=−4.4 mmu); $^1$H and $^{13}$C NMR data, see Table 1.

HRFABMS data for carbonarin A showed a pseudomolecular (M+H)$^+$ ion at m/z 583.1649 suggesting the molecular formula $C_{33}H_{26}O_{10}$. The $^1$H NMR spectrum (in acetone-$d_6$) showed the presence of para-disubstituted, 1, 2, 4-trisubstituted, and 1, 2, 3, 5-tetrasubstituted benzenoid rings, along with two methoxy groups, one aryl methyl gwup, an isolated methylene group, an oxymethine unit, and an isolated vinylic proton. Two exchangeable phenolic OH signals were also observed at 15.13 and 8.25 ppm.

Treatment of carbonarin A with acetic anhydride in pyridine resulted in formation of a triacetate derivative, indicating that carbonarin A contains at least three hydroxy groups. Changes in the $^1$H NMR spectrum of this derivative showed that the para-disubstituted and 1, 2, 4-trisubstituted aromatic rings contain phenolic OH groups, and that the oxymethine unit is present as a CHOH group in the natural product. The $^{13}$C NMR and DEPT data for carbonarin A contained signals for these units, as well as a doubly conjugated ketone functionality and nine other non-protonated sp$^2$ carbons not accounted for by the units listed above.

Analysis of NOESY, HMBC [Summers, 1986], and HMQC [Bax, 1986] data (Table 1), and comparison of the NMR chemical shifts and UV data (maxima at 225, 280,and 410 nm) with literature values suggested the presence of a linear 6-hydroxy-8,10-dimethoxy-2-methyl-4H-naphtho[2, 3b]pyran-4-one moiety as part of structure 1 [Priestap, 1986; Gorst-Allman, 1980]. The IR spectrum of carbonarin A exhibited an absorption band at 1652 cm$^{-1}$, as expected for the carbonyl group of the pyrone system.

The connectivity of the 6-hydroxy-8, 10-dimethoxy-2-methyl-4H-naphtho[2, 3b] pyran-4-one system with the 1,2, 4-tetrasubstituted aromatic ring through the C-13-C-15 bond was established on the basis of I-IMBC correlations (Table 1) of both H-11 and H-20 with the signal for the non-protonated sp$^2$-hybridized carbon C-13. This connectivity was supported by an intense NOESY correlation between H-11 and H-20. The regiochemistry and $^{13}$C NMR assignments for these two subunits were determined by analysis of HMBC and selective INEPT [Bax, 1984] data (Table 1).

The aromatic proton signal for H-28/H-32 showed an HMBC correlation with the signal for the aliphatic methylene carbon (C-26), indicating connection of C-26 with C-27. In addition, the IR and 3C NMR spectra of carbonarin A suggested the presence of an ester carbonyl (1759 cm$^{-1}$; 171.4 ppm). Thus, at this point, one CHOH group, a para-hydroxybenzyl unit, one ester group, two additional sp$^2$ carbon atoms (129.2 and 157.1 ppm), and two unsaturations remained to be assigned. Connectivity of these units was established with the aid of HMBC and selective INEPT correlations (Table 1). The signals for H-18 and H-20 showed strong HMBC and selective INEPT correlations with the olefinic carbon signal at 129.2 ppm (C-21). These correlations allowed connection of C-19 of the 1, 2, 4-trisubstituted aromatic ring with the olefinic carbon C-21. The benzylic protons H$_2$-26 of the para-hydroxybenzyl moiety showed selective INEPT correlations with resonances for the same olefinic carbon (C-21), the olefinic carbon signal at 158.7 ppm (C-25), and the acetal carbon C-24 (97.6 ppm). These results revealed that both the benzylic carbon C-26 and the acetal carbon C-24 must be linked to the olefinic carbon C-25. Irradiation of the acetal CH proton in selective INEPT experiments resulted in polarization transfer to C-21 and C-25, and to the carboxyl carbon C-22. These findings indicated the linkage of the acetal carbon C-24 to the olefinic carbon C-25 and the ester oxygen to afford the trisubstituted 2 (5H)-furanone system. Based on all of these results and on chemical shift considerations, the structure of carbonarin A was assigned.

Carbonarin B $t_R$ 26.2 min; $[\alpha]_D$=0° (0.08 g/dL); $[\alpha]_{Hg}$=−10.8° (0.08 g/dL); UV (MeOH) 241 nm ($\epsilon$=21000), 285 nm ($\epsilon$=15300), 370 nm ($\epsilon$=3100); LRFABMS (3-NBA) ions at m/z 583 ([M+H]$^+$,10), 565 (1), 279 (3), 256 (2), 219 (3), 205 (1), 165 (5); HRFABMS (glycerol), obsd, 583.1612 (M+H); calcd for C$_{33}$H$_{26}$O$_{10}$+H, 583.1604 ($\Delta$=−0.8 mmu); $^1$H and $^{13}$C NMR data, see Table 2.

The second novel antiinsectan metabolite isolated was carbonarin B. Analysis of the $^1$H NMR, $^{13}$C NMR, and HRFABMS data for carbonarin B indicated that it is a regioisomer of carbonarin A. The difference between these two isomers was suggested by comparison of their UV spectra and the chemical shifts of the C-6 phenolic OH proton NMR signals for carbonarin A and carbonarin B. The UV absorptions of carbonarin B were located at 241, 282, and 370 nm and were characteristic of an angular naphtho-γ-pyrone. The bent character of the naphtho-γ-pyrone subunit was also indicated by the upfield shift of the C-6 OH proton signal (13.36 ppm, vs. 15.13 ppm for carbonarin A) which is typical for angular naphthopyrones [Priestap, 1984]. Confirmatory evidence for the presence of an angular naphthopyrone in carbonarin B was provided by analysis of the HMBC data (Table 2). The H-bonded exchangeable proton (OH-6) and H-3 each showed strong HMBC correlations with the signal for C-5 (109.2). Also, OH-6 and H-9 exhibited HMBC correlations with the resonance at 113.3 ppm (C-7). An additional HMBC correlation for OH-6 was observed with the signal for the oxygenated carbon C-6. These results verified that the hydroxy group is attached to C-6,and that the naphthopyrone unit must have the angular geometry. The regiochemistry of the trisubstituted aromatic ring and the furanone moiety of carbonarin B was confirmed by further analysis of the HMBC data (Table 2), which gave results analogous to those observed for carbonarin A.

An interesting feature of the $^1$H NMR spectra of carbonarin A and carbonarin B was the doubling of certain signals at room temperature (298° K.). In the spectrum of carbonarin A, the H$_3$-33 and H$_3$-35 signals appeared as doubled singlets while the rest of the spectrum showed the expected multiplicities. On the other hand, the spectrum of the angular naphtho-γ-pyrone of carbonarin B showed a doubling of all signals except the resonance for H$_3$-33, which resonated as one singlet, possibly due to fortuitous overlap. A variable-temperature study of the proton NMR behavior of carbonarins A and B was performed to test this possibility. Upon elevating the temperature to 320° K. (47° C.), the signals attributed to H$_3$-33 and H$_3$-35 of compound 1 coalesced to broad singlets. However, when the carbonarin A was cooled to 240° K., all signals in the $^1$H NMR spectrum showed doubling. By contrast, no changes were observed in the $^1$H NMR spectrum of carbonarin B at either temperature. These observations show that the doubling of signals in these compounds is likely due to restricted rotation around the C-13-C-15 single bond, in combination with the presence of a chiral center at C-24. The H$_3$-33 and H$_3$-35 signals for carbonarin A are doubled at room temperature because their chemical shifts are presumably influenced to a greater degree than the other signals by the difference between the rotamers. As the temperature is lowered, the doubled signals gradually move further apart, with $\Delta\delta$ changing from 0.02 ppm at 298° K. to 0.06 ppm at 240° K. Signals not doubled at room temperature gradually resolve into doubled signals with $\Delta\delta$ values ranging from 0.01 to 0.04 ppm at 240° K. The presence of the chiral center at C-24 in each compound is consistent with an NMR difference between conformers, since the atropisomers would be diastereomeric.

The naphthopyrone portion of these compounds is likely to be of polyketide origin, and matches structural units of the aurasperones previously reported from A. niger. However, the furanone-containing portion appears to arise from the shikimate pathway, possibly forming through condensation of two moles of parahydroxyphenylpyruvate, accompanied by decarboxylation and reduction steps [Turner, 1983].

The structures for carbonarins C, D, E, F, G, and H were determined through processes as described above and by analogy to the structures of carbonarins A and B. In concert with the NMR discussion above, carbonarins lacking the chiral center (OH substituent) at C-24 showed no doubling of signals in their proton NMR spectra. Relevant data are presented below and in the tables herein.

Carbonarin C:

$t_R$ 22.2 min; $[\alpha]_D$=0° (0.08 g/dL); $[\alpha]_{Hg}$=0° (0.08 g/dL); UV (MeOH) 228 nm ($\epsilon$=23400), 280 nm ($\epsilon$=18500) 410 nm ($\epsilon$=2900); LRFABMS (glycerol) ions at m/z 566 ([M+H]$^+$, 4), 462 (2), 432 (1), 333 (2), 313 (1), 302 (3), 297 (4), 286 (11), 279 (3), 273 (2), 257 (3), 227 (3), 171 (2), 165 (6); HRFABMS (glycerol), obsd, 566.1804 (M+H); calcd for $C_{33}H_{27}NO_8$+H, 566.1815 (Δ=1.1 mmu); $^1H$ and $^{13}C$ NMR data, see Table 3.

Carbonarin D:

$t_R$ 30.5 min; $[\alpha]_D$=0° (0.08 g/dL); $[\alpha]_{Hg}$=0° (0.08 g/dL); UV (MeOH) 244 nm (ε=17400), 285 nm (ε=11500), 380 nm (ε=2800); LRFABMS (3-NBA) ions at m/z at 566 ([M+H]$^+$, 2), 301 (2), 279 (3), 273 (2), 256 (2), 219 (3), 192 (2), 165 (5); HRFABMS (glycerol), obsd. 566.1812 (M+H); calcd for $C_{33}H_{27}NO_8$+H, 566.1815 (Δ=0.3 mmu); $^1H$ and $^{13}C$ NMR data, see Table 4.

Carbonarin E:

$t_R$ 7.7 min; $[\alpha]_D$=0° (0.08 g/dL); $[\alpha]_{Hg}$=0° (0.08 g/dL); UV (MeOH) 225 nm (ε10200), 280 nm (ε=5800), 371 nm (ε=1100); LRFABMS (3-NBA) ions at m/z 312 ([M+H]$^+$, 15), 242 (7), 235 (7), 219 (13), 165 (26) 138 (100); HRFABMS (3-NBA), obsd. 312.1255 (M+H); calcd for $C_{18}H_{18}NO_4$+H, 312.1236 (Δ=-1.9 mmu); $^1H$ and $^{13}C$ NMR data, see Table 5.

Isolation and Identification of Carbonarins F, G, and H

As discussed above, the MeOH extract of ground sclerotia was partitioned between $H_2O$ (1 L) and $CHCl_3$ (4×1 L). The resulting organic extracts were combined, evaporated under reduced pressure, and redissolved in 10% $H_2O$/MeOH. This mixture was extracted with hexane (4×2 L) to remove nonpolar, inactive material. The aqueous MeOH fraction was evaporated under reduced pressure to afford a yellowish residue (1.14 g) which was fractionated on a Si gel flash column (100 g of $GF_{254}$; 60–200 mesh; Fluka) using increasing concentrations of MeOH in $CHCl_3$. This column afforded six fractions. Fraction 1 (430.2 mg), obtained at 5% MeOH—$CHCl_3$(4×500 mL) from the flash Si gel column described above, was subjected to preliminary separation by chromatography on Sephadex LH-20 (25–100μ; Sigma Chemical Co.) using a hexane: toluene: MeOH (3: 2: 1) solvent system. Isocratic elution of the column afforded five fractions. Fraction 5 (60 mg) was further purified on a Si gel column (15 g of $GF_{254}$; 60–200 mesh; Fluka) using a step gradient from 100% $CHCl_3$ to 100% MeOH to obtain 31 fractions. Similar fractions (as shown by TLC) were combined. Fractions 1–4 were eluted with $CHCl_3$ to obtain a mixture which contained a major component. This mixture was further purified on preparative HPLC using 70% MeOH—$H_2O$ to yield carbonarin G (2.6 mg). Carbonarin H (3.9 mg) was obtained at 5% MeOH/$CHCl_3$ (Fractions 9–14). Fractions 21–24 were eluted from the column with 10% MeOH/$CHCl_3$, and contained pure carbonarin F (5.5 mg).

Carbonarin F:

$[\alpha]_D$=0° (0.08 g/dL); $[\alpha]_{Hg}$=-9.6° (0.08 g/dL); UV (MeOH) 228 nm (ε18800), 280 nm (ε17000), 410 nm (ε2700); LRFABMS (glycerol) ions at m/z 613 ([M+H]$^+$, 48), 597 (3), 539 (1), 477 (1), 423 (1), 363 (1), 333 (2), 297 (2), 286 (3), 272 (2), 263 (2), 257 (3), 239 (2), 205 (2), 165 (6); HRFABMS (glycerol), obsd. 613.1721 (M+H); calcd for $C_{34}H_{28}O_{11}$+H, 613.1710 (Δ=-1.1 mmu); $^1H$ and $^{13}C$ NMR data, see Table 6.

Carbonarin G:

$[\alpha]_D$=0° (0.08 g/dL); $[\alpha]_{Hg}$=0° (0.08 g/dL); UV (MeOH) 228 nm (ε14,900), 280 nm (ε13800), 410 nm (ε=1900); $^1H$ and $^{13}C$ NMR data, see Table 7.

Carbonarin H:

$[\alpha]_D$=0° (0.08 g/dL); $[\alpha]_{Hg}$=0° (0.08 g/dL); UV (MeOH) 228 nm (ε=14900), 280 nm (ε12600), 410 nm (ε2300); LRFABMS (3-NBA) ions at m/z 567 ([M+H]$^+$, 5), 341 (0.6), 309 (0.9), 273 (2), 260 (0.8), 257 (1), 242 (1), 235 (1), 226 (1), 223 (0.9), 219 (3), 205 (2), 195 (0.9), 180 (1), 167 (3); HRFABMS (glycerol), obsd. 567.1641 (M+H); calcd for $C_{33}H_{26}O_9$+H, 567.1655 (Δ=1.4 mmu); $^1H$ NMR data, see Table 8.

Example 2: Insecticidal Activity of Carbonarins A, B, C, D, E, F, G, and H

The carbonarin compounds of the present invention were evaluated by insect bioassays described previously by Dowd in *Entomol. Exp. Appl.* 47:69 (1988) and Wicklow, et al. in *Trans. Br. Mycol. Soc.* 91:433 (1988). Neonam larvae of *H. zea*, second instar (ca. 0.75 rag) larvae of *C. hemipterus* and adults of *C. hemipterus* were used for all assays. They were obtained from laboratory colonies reared on a pinto bean-based diet at 27° C.±1° C., 40±10% relative humidity, and a 14:10 light:dark photo period.

The diet used to rear the insects was based on a standard pinto bean diet for many species, which contains the following ingredients: 120 g dried pinto beans, 43 g wheat germ, 28 g brewer's yeast, 8 g Vanderzant's vitamin mix, 2.8 g ascorbic acid, 1.75 g methyl paraben, 0.9 g sorbic acid, 12 g agar, 2 mL formaldehyde (38%), 1.5 mL of propionic-phosphoric acid solution (42% propionic acid, 4.2% phosphoric acid), and 550 mL water. All dry diet ingredients (except for the pinto beans) were purchased from U.S. Biochemicals Corp. Before use, the beans were soaked in water until saturated (overnight). The agar was added to 250 mL of water and brought to a boil. The other ingredients were blended in a Waring blender until uniformly mixed. The hot agar was added, and blending continued until all ingredients were uniformly The pinto bean-based diet thus prepared was added in 5-ml quantities to test tubes. The test tubes were held at 60° C. until chemicals were incorporated to prevent solidification of the diet. A carbonarin compound of the present invention was added in 125 μL of acetone to the liquid diet to give a final concentration of typically 100 ppm. Upon addition of the compound, the mixture was removed from the water bath. The carbonarin compound was incorporated into the diets by blending vigorously with a vortex mixer for 20 sec. Preliminary observations with colored solutions of both water and acetone indicated uniform incorporation by this method. The diets were dispensed into culture plates and allowed to cool to room temperature. To remove the potentially toxic acetone, the diets were placed in a fume hood for ca. 20 rain until slight darkening occurred. The diets were cut into approximately equal sections, and each section was placed into a well of a 24-well immunoassay plate. A single neonate *H. zea* or five *C. hemipterus* larvae or adults was added to each well. To prevent desiccation of the diet, the plate was covered by a sheet of parafilm, a sheet of cardboard, and the plastic cover. The cover was secured by two rubber bands, and groups of plates were placed in two polyethylene bags held closely by rubber bands. The plates were held under the same conditions used to rear the insects. Mortality was checked at 2, 4 and 7 days, and the surviving larvae were weighed after 7 days. Each carbonarin compound was tested on a total of 20 larvae. Diet feeding rating for *C. hemipterus* larvae was based on a scale of 1 (limited to no feeding) to 4 (diet thoroughly tunneled or pulverized) [Wicklow et at., supra (1988)].

Carbonarin A caused a 31% feeding reduction by *C. hemipterus* adults when incorporated into a standard pinto bean test diet at 100 ppm, but did not affect *H. zea* in dietary assays at the same concentration.

All carbonarins, except D and E, were effective in reducing the feeding rate in driedfruit beetle adults (*Carpophilus*

*hemipterus*). The effect in the feeding rate of carbonarins D and E have not yet been tested. Carbonarins G and H reduced the feeding ram for driedfruit beefle larvae. The effect of Carbonarins B, C, D, E and F on the feeding rate driedfruit beetle larvae have not yet been tested. Carbonarins B and E also successfully reduced the growth rate in corn earworm larvae (*Helicoverpa zea*). These data are summarized in Table 9 below.

Carbonarins B, C, F, G, and H were determined to be effective as an antiinsectan against fall armyworms (*Spodoptera frugiperda*) in a leaf disk assay. Two cm diameter dish were cut from fully expanded cotton leaves. They were placed on top of a 3.5 cm diameter piece of filter paper placed in the bottom of a 3.5 cm diameter culture plate. 25 microliters of a 1 mg/mL acetone solution of the compound was applied and spread on each side of the disk with a pipettor. Acetone alone served as the control. Five disks were used for each treatment. Ten newly hatched fall armyworms larvae were added to each disk. The culture plate cover was replaced and sealed with a strip of parafilm. Plates were examined after two days to determine the number of dead caterpillars and the degree of damage. Damage was rated on a 1–10 scale with 1=0–10% of the leaf eaten, 2= approximately 20% of the leaf eaten, 3= approximately 30% of the leaf eaten, and so on. Reduction in damage was calculated relative to mean damage incurred by the control disks. Table 10 summarizes these results.

TABLE 2

NMR Data For Carbonarin B

| position | multiplicity $^1$HH | $\delta$_H | $\delta$ C | HMBC | NOESY |
|---|---|---|---|---|---|
| 1 | — | — | — | — | — |
| 2 | — | — | 168.4 | — | — |
| 3 | brs | 6.39 | 110.8 | 2, 5, 33 | 33 |
| 4 | — | — | 183.8 | — | — |
| 5 | — | — | 109.2 | — | — |
| 6 | | | 158.7 | | |
| 7 | — | — | 105.3 | — | — |
| 8 | — | — | 160.8 | — | — |
| 9 | d, 2.1 | 6.56 | 97.9 | 7, 8, 10, 11 | 234, 35 |
| 10 | — | — | 162.8 | | |
| 11 | d, 2.1 | 6.49 | 98.3 | 7, 9, 10, 13 | 20, 29, 31, 35 |
| 12 | — | — | 141.7 | — | — |
| 13 | — | — | 113.3 | — | — |
| 14-OH | s | 13.36 | 156.8 | 5, 13, 14 | — |
| 15 | — | — | 122.5 | — | — |
| 16 | — | — | 157.1$^b$ | — | — |
| 17 | d, 8.4 | 7.13 | 117.2 | 15, 16, 19 | 18 |
| 18 | dd, 2.2, 8.4 | 7.52 | 131.1 | 16, 20, 21 | 17, 26α, 26β, 28 |
| 19 | — | — | 123.5 | — | |
| 20 | d, 2.2 | 7.42 | 134.6 | 13, 16, 18, 21 | 11, 26α, 28 |
| 21 | — | — | 129.6 | — | — |
| 22 | — | — | 171.2 | — | — |

TABLE 1

| Position | Multiplicity $^1$HH | $\delta$ H | $\delta$ H$^a$ | $\delta$ C | $\delta$ C$^b$ | HMBC | Selective INEPT | HMBC$^c$ | NOESY |
|---|---|---|---|---|---|---|---|---|---|
| 1 | — | — | — | — | — | — | — | — | — |
| 2 | — | — | — | 169.2 | 170.3 | — | — | — | — |
| 3 | s | 6.07 | 5.95 | 107.6 | 107.7 | 2, 5, 33 | — | 2, 5, 33 | 33 |
| 4 | — | — | — | 185.4 | 186.2 | — | — | — | — |
| 5 | — | — | — | 104.7 | 104.9 | — | — | — | — |
| 6-OH | s | 15.13 | — | 164.0 | 163.1 | 5, 6, 7 | 5, 6, 7 | — | — |
| 7 | — | — | — | 109.3 | 109.4 | — | — | — | — |
| 8 | — | — | — | 162.7 | 162.2 | — | — | — | — |
| 9 | brs | 6.48 | 6.37 | 97.5 | 98.3 | 7, 8, 10, 11* | — | 7, 8, 10, 11 | 34, 35 |
| 10 | | — | | 162.7 | 162.2 | — | | — | |
| 11 | brs | 6.48 | 6.37 | 97.48 | 97.8 | 7, 9, 10, 13 | — | 7, 9, 10, 13 | 20, 29, 35 |
| 12 | — | — | — | 141.4 | 141.8 | — | — | — | — |
| 13 | — | — | — | 109.1 | 110.8 | — | — | — | — |
| 14 | — | — | — | 151.8 | 151.8 | — | — | — | — |
| 15 | — | — | — | 122.3 | 122.3 | — | — | — | — |
| 16 | — | — | — | 157.1 | 157.5 | — | — | — | — |
| 17 | d, 8.4 | 7.16 | 7.02 | 117.1 | 117.2 | 15, 16, 19 | 15, 16, 19 | 15, 16, 19 | 18 |
| 18 | dd, 2.3, 8.4 | 7.57 | 7.35 | 131.2 | 131.5 | 16, 20, 21 | 16, 20, 21 | 16, 20, 21 | 17, 28 |
| 19 | | — | | 122.4 | 123.1 | — | | — | |
| 20 | d, 2.3 | 7.45 | 7.30 | 134.6 | 135.0 | 13, 16, 18, 21 | 13, 16, 18, 21 | 13, 16, 18, 21 | 11, 28 |
| 21 | — | — | — | 129.2 | 129.6 | — | — | — | — |
| 22 | s | 5.93 | 5.77 | 97.6 | 98.7 | 23 | 21, 23, 25 | 23 | — |
| 23 | — | — | — | 171.4 | 173.3 | — | — | — | — |
| 24 | — | — | — | — | — | — | — | — | — |
| 25 | — | — | — | 157.1 | 160.2 | — | — | — | — |
| 26α | d, 14.4 | 3.78 | — | 32.4 | 32.6 | — | 21, 25, 27, 28 22, 27, 28 | — | 26β |
| 26β | d, 14.4 | 4.09 | — | | | | | | 26α |
| 27 | — | — | — | 128.3 | 128.5 | — | — | — | — |
| 28 | d, 8.5 | 7.06 | 6.91 | 130.7 | 130.9 | 26, 30, 32 | — | 26, 30, 32 | 18, 20, 22, 29 |
| 29 | d, 8.5 | 6.73 | 6.58 | 116.4 | — | 27, 30, 31 | — | 27, 30, 31 | 11, 28 |
| 30 | — | — | — | 158.7 | 157.6 | — | — | — | — |
| 31 | d, 8.5 | 6.73 | — | 116.4 | — | 27, 29, 30 | — | 27, 29, 30 | — |
| 32 | d, 8.5 | 7.06 | — | 130.7 | — | 26, 28, 30 | — | 26, 28, 30 | — |
| 33 | s | 2.22$^d$ | 2.10 | 20.4 | 20.5 | — | — | 2, 3 | 8 |
| 34 | s | 3.95 | 3.83 | 56.3 | 56.5 | 8 | — | 3 | 9 |
| 35 | s | 3.67$^d$ | 3.56 | 55.5 | 55.6 | — | 10 | 10 | 11 |

$^a$300 MHz. $^b$75 MHz. $^c$600 MHz. $^d$These resonances appeared as doubled signals at room temperature. Their chemical shifts are reported as average sales. $\Delta\delta$ values for double proton signals ranged from 0–0.06 ppm.

TABLE 2-continued

NMR Data For Carbonarin B

| position | multiplicity $J_{HH}$ | $\delta\_H$ | $\delta C$ | HMBC | NOESY |
|---|---|---|---|---|---|
| 23 | — | — | — | — | — |
| 24 | s | 5.91 | 97.7 | 22 | 28, 32 |
| 25 | — | — | 158.7 | — | — |
| 26α | d, 15.1 | 3.76 | 32.4 | 21, 24, 25, 28 | 18, 20, 28, 26β, 32 |
| 26β | d, 15.1 | 4.11 | | 21, 24, 25, 28 | 18, 26α, 28 |
| 27 | — | — | 128.6 | — | — |
| 28 | d, 8.5 | 7.08 | 130.8 | 26, 30, 32 | 18, 20, 24, 26α, 26β, 29, 31 |
| 29 | d, 8.5 | 6.74 | 116.6 | 27, 30, 31 | 11, 28, 32 |
| 30 | — | — | 157.2[b] | — | — |
| 31 | d, 8.5 | 6.74 | 116.6[b] | 27, 29, 30 | 11, 28, 32 |
| 32 | d, 8.5 | 7.08 | 130.8 | 26, 28, 30 | 18, 20, 24, 26α, 26β, 29, 31 |
| 33 | s | 2.56 | 20.4 | 2, 3 | 3 |
| 34 | s | 4.05 | 56.8 | 8 | 9 |
| 35 | s | 3.69 | 55.7 | 10 | 9, 11 | a. All resonances except those for H₃-33 appeared as doubled signals at room temperature. Their chemical shifts are reported as average values. Δδ values for doubled proton signals ranged from 0–0.09 pm.
[b]These assignments may be interchanged.

TABLE 3

NMR Data For Carbonarin C

| position | multiplicity $J_{HH}$ | $\delta\_H$ | $\delta C$ | HMBC |
|---|---|---|---|---|
| 1 | — | — | — | — |
| 2 | — | — | 168.7 | — |
| 3 | br s | 6.06 | 107.2 | 2, 5, 33 |
| 4 | — | — | 185.0 | — |
| 5 | — | — | 104.3 | — |
| 6-OH | s | 15.13 | 162.5 | 5, 6, 7 |
| 7 | — | — | 109.7 | — |
| 8 | — | — | 161.4 | — |
| 9 | d, 2.2 | 6.47 | 97.5 | 7, 8, 10, 11 |
| 10 | — | — | 162.1 | — |
| 11 | d, 2.2 | 6.55 | 97.2 | 7, 9, 10, 13 |
| 12 | — | — | 141.0 | — |
| 13 | — | — | 108.7 | — |
| 14 | s | | 151.1 | — |
| 15 | — | — | 121.5 | — |
| 16 | — | — | 155.6 | — |
| 17 | d, 8.2 | 7.17 | 116.3 | 15, 16, 19 |
| 18 | dd, 2.1, 8.2 | 7.55 | 130.8 | 16, 20, 21 |
| 19 | — | — | 123.7 | — |
| 20 | d, 2.1 | 7.43 | 134.1 | 13, 16, 18, 21 |
| 21 | — | — | 132.4 | — |
| 22 | — | — | 174.6 | — |
| 23 | — | — | — | — |
| 24α | s | 3.84 | 47.8 | 21, 25 |
| 24β | s | 3.84 | | 21, 25 |
| 25 | — | — | 153.7 | — |
| 26α | s | 3.90 | 34.1 | 21, 24, 25, 28, 32 |
| 26β | s | 3.90 | | 21, 24, 25, 28, 32 |
| 27 | — | — | 129.2 | — |
| 28 | d, 8.5 | 7.02 | 129.8 | 26, 30, 32 |
| 29 | d, 8.5 | 6.74 | 115.9 | 27, 30, 31 |
| 30 | — | — | 156.4 | — |
| 31 | d, 8.5 | 6.74 | 115.9 | 27, 29, 30 |
| 32 | d, 8.5 | 7.02 | 129.8 | 26, 28, 30 |
| 33 | s | 2.2 | 20.4 | 2, 3 |
| 34 | s | 3.95 | 56.2 | 8 |
| 35 | s | 3.67 | 55.2 | 10 |

TABLE 4

NMR Data For Carbonarin D

| position | multiplicity $J_{HH}$ | $\delta\_H$ | HMBC |
|---|---|---|---|
| 1 | — | — | — |
| 2 | — | — | — |
| 3 | br s | 6.36 | 2, 5, 33 |
| 4 | — | — | — |
| 5 | — | — | — |
| 6 | — | — | — |
| 7 | — | — | — |
| 8 | — | — | — |
| 9 | br s | 6.52 | 7, 8, 10, 11 |
| 10 | — | — | — |
| 11 | br s | 6.52 | 7, 9, 10, 13 |
| 12 | — | — | — |
| 13 | — | — | — |
| 14-OH | s | 13.33 | 5, 13, 14 |
| 15 | — | — | — |
| 16 | — | — | — |
| 17 | d, 8.4 | 7.35 | 15, 16, 19 |
| 18 | dd, 2.0, 8.4 | 7.47 | 16, 20, 21 |
| 19 | — | — | — |
| 20 | d, 2.0 | 7.06 | 13, 16, 18, 21 |
| 21 | — | — | — |
| 22 | — | — | — |
| 23 | — | — | — |
| 24α | br s | 3.85 | 22 |
| 24β | br s | 3.85 | |
| 25 | — | — | — |
| 26α | s | 3.85 | 21, 24, 25, 28 |
| 26β | s | 3.85 | 21, 24, 25, 28 |
| 27 | — | — | — |
| 28 | d, 8.4 | 7.00 | 26, 30, 32 |
| 29 | d, 8.4 | 6.69 | 27, 30, 31 |
| 30 | — | — | — |
| 31 | d, 8.4 | 6.69 | 27, 29, 30 |
| 32 | d, 8.4 | 7.00 | 26, 28, 30 |
| 33 | s | 2.54 | 2, 3 |
| 34 | s | 4.02 | 8 |
| 35 | s | 3.62 | 10 |

TABLE 5

NMR Data For Carbonarin E

| position | multiplicity $J_{HH}$ | $\delta\_H$ | $\delta C$ | HMBC | NOESY |
|---|---|---|---|---|---|
| 1 | — | — | — | — | — |
| 2 | — | — | 174.0 | — | — |
| 3 | — | — | 132.8 | — | — |
| 4 | — | — | 152.9 | — | — |
| 5α | s | 3.84 | 48.2 | 4, 5 | 6" |
| 5β | s | 3.84 | | 4, 5 | 6" |
| 6α | s | 3.83 | 34.8 | 1", 2", 3, 4, 5, 6" | 2', 2" |
| 6β | s | 3.83 | | 1", 2", 3, 4, 5, 6" | 2', 2" |
| 1' | — | — | 124.4 | — | — |
| 2' | d, 8.6 | 7.41 | 131.4 | 3', 4, 4', 6' | 3', 2", 6, 6" |
| 3' | d, 8.6 | 6.88 | 115.8 | 1', 4', 5' | 2' |
| 4' | — | — | 157.9 | — | — |
| 5' | — | — | 115.8 | — | — |
| 6' | — | — | 131.4 | — | — |
| 1" | — | — | 130.6 | — | — |
| 2" | d, 1.9 | 6.77 | 113.0 | 1", 3", 4", 6, 6" | 2', 6, 7" |
| 3" | — | — | 148.5 | — | — |
| 4" | — | — | 146.2 | — | — |
| 5" | d, 7.8 | 6.76 | 115.8 | 1", 3", 4", 6" | 6" |
| 6" | dd, 1.9, 7.8 | 6.66 | 121.8 | 2", 4", 6 | 2', 3, 5" |
| 7" | s | 3.78 | 56.2 | 3" | 2" |

TABLE 6

NMR Data For Carbonarin F

| position | multiplicity $J_{HH}$ | δ*H | ΔδH | δ C | HMBC |
|---|---|---|---|---|---|
| 1 | — | — | — | — | — |
| 2 | — | — | — | 169.2 | — |
| 3 | brs | 6.07 | 0.018 | 107.6 | 2, 5, 33 |
| 4 | — | — | — | 185.4 | — |
| 5 | — | — | — | 104.7 | — |
| 6-OH | s | 15.14 | 0.006 | 164.0 | 5, 6, 7 |
| 7 | — | — | — | 109.3(b) | — |
| 8 | — | — | — | 162.3 | — |
| 9 | brs | 6.48 | 0.020 | 97.6 | 7, 8, 10, 11 |
| 10 | — | — | — | 162.8 | — |
| 11 | brs | 6.48 | 0.025 | 97.6 | 7, 9, 10, 13 |
| 12 | — | — | — | 141.4 | — |
| 13 | — | — | — | 109.1c | — |
| 14 | — | — | — | 151.8 | — |
| 15 | — | — | — | 122.2(e) | — |
| 16-OH | s | 8.23 | 0 | 157.2 | 15, 16, 17 |
| 17 | d, 8.5 | 7.17 | 0 | 117.2 | 15, 16, 19 |
| 18 | dd, 2.1, 8.5 | 7.59 | 0.020 | 131.3 | 16, 20, 21 |
| 19 | — | — | — | 122.4 | — |
| 20 | d, 2.1 | 7.46 | 0.009 | 134.6 | 13, 16, 18, 21 |
| 21 | — | — | — | 129.3 | — |
| 22 | — | — | — | 171.2 | — |
| 23 | — | — | — | — | — |
| 24 | d, 8.0 | 5.98 | 0.062 | 97.5 | 22 |
| 24-OH | d, 8.0 | 6.74 | 0.017 | | 24, 25 |
| 25 | — | — | — | 158.6 | — |
| 26α | d, 15.0 | 3.77 | 0.043 | 32.7 | 21, 24, 25, 28, 32 |
| 26β | d, 15.0 | 4.08 | 0.033 | | 21, 24, 25, 28, 32 |
| 27 | — | — | — | 128.7 | — |
| 28 | d, 1.8 | 6.80 | — | 113.2 | 26, 27, 29, 30, 32 |
| 29 | — | — | — | 148.5 | — |
| 30-OH | s | 7.48 | 0.003 | 145.5 | 29, 30, 31 |
| 31 | d, 8.0 | 6.71 | 0.017 | 116.0 | 27, 29, 30 |
| 32 | dd, 1.8, 8.0 | 6.67 | 0.024 | 122.1(d) | 26, 28, 30 |
| 33 | s | 2.20 | 0.040 | 20.4 | 2, 3 |
| 34 | s | 3.95 | 0.006 | 56.4 | 8 |
| 35 | s | 3.63 | 0.052 | 55.5 | 10 |
| 36 | s | 3.68 | 0.034 | 56.2 | 29 |

6. 600 MHz. All resonances appeared as doubled signals at room temperature except H-17 and HO-16. All doubled signals have the same multiplicities except H-9 and H-11 which resonated as an overlapped broad singlet (6.48 ppm) in one set and two resolved doublets (6.469 and 6.474 ppm, J=2.0Hz) in the second set. Chemical shifts are reported as average values. b,c;d,e. These assignments may be interchanged.

TABLE 7

NMR Data For Carbonarin G in CDCl₃

| position | multiplicity $J_{HH}$ | δ_H | δ C | HMBC |
|---|---|---|---|---|
| 1 | — | — | — | — |
| 2 | — | — | 168.2 | — |
| 3 | brs | 5.93 | 107.3 | 2, 5, 33 |
| 4 | — | — | * | — |
| 5 | — | — | 103.7 | — |
| 6-OH | s | 15.17 | 163.1 | 5, 6, 7 |
| 7 | — | — | 108.5 | — |
| 8 | — | — | 160.8 | — |
| 9 | d, 2.1 | 6.39 | 97.5 | 7, 8, 10, 11 |
| 10 | — | — | 162.6 | — |
| 11 | d, 2.1 | 6.30 | 96.3 | 7, 9, 10, 13 |
| 12 | — | — | * | — |
| 13 | — | — | 105.7 | — |
| 14 | — | — | * | — |
| 15 | — | — | 121.6* | — |
| 16 | — | — | 154.7 | — |
| 17 | d, 8.5 | 7.21 | 116.2 | 15, 16, 19 |
| 18 | dd, 2.1, 8.5 | 7.59 | 130.6 | 16, 20, 21 |
| 19 | — | — | 121.2* | — |
| 20 | d, 2.1 | 7.38 | 133.1 | 13, 16, 18, 21 |
| 21 | — | — | 126.5 | — |
| 22 | — | — | 173.9 | — |
| 23 | — | — | — | — |
| 24α | s | 4.65 | 71.1 | 21, 22, 25 |
| 24β | s | 4.65 | | 21, 22, 25 |
| 25 | — | — | 159.2 | — |
| 26α | s | 3.87 | 33.5 | 21, 24, 25, 27, 28, 32 |
| 26β | s | 3.87 | | 21, 24, 25, 27, 28, 32 |
| 27 | — | — | 128.2 | — |
| 28 | d, 1.8 | 6.54 | 110.6 | 26, 29, 30, 32 |
| 29 | — | — | 146.9 | — |
| 30-OH | s | 5.52 | 144.9 | 29, 30, 31 |
| 31 | d, 8.1 | 6.81 | 115.1 | 27, 29, 30 |
| 32 | dd, 1.8, 8.1 | 6.66 | 121.2* | 26, 28, 30 |
| 33 | s | 2.51 | 20.4 | 2, 3 |
| 34 | s | 3.89 | 56.2 | 8 |
| 35 | s | 3.68 | 55.2 | 10 |
| 36 | s | 3.73 | 56.6 | 29 |

*These assignments may be interchanged.

TABLE 8

NMR Data For Carbonarin H

| position | multiplicity $J_{HH}$ | $δ_H^1$ |
|---|---|---|
| 1 | — | — |
| 2 | — | — |
| 3 | br s | 6.07 |
| 4 | — | — |
| 5 | — | — |
| 6-OH | s | 15.14 |
| 7 | — | — |
| 8 | — | — |
| 9 | br s | 6.50 |
| 10 | — | — |
| 11 | br s | 6.49 |
| 12 | — | — |
| 13 | — | — |
| 14 | — | — |
| 15 | — | — |
| 16 | — | — |
| 17 | d, 8.3 | 7.17 |
| 18 | dd, 2.2, 8.3 | 7.57 |
| 19 | — | — |
| 20 | d, 2.2 | 7.45 |
| 21 | — | — |
| 22 | — | — |
| 23 | — | — |
| 24α | s | 4.72 |
| 24β | s | 4.72 |
| 25 | — | — |
| 26α | s | 4.05 |
| 26β | s | 4.05 |
| 27 | — | — |
| 28 | d, 8.2 | 7.05 |
| 29 | d, 8.2 | 6.75 |
| 30 | — | — |
| 31 | d, 8.2 | 6.75 |
| 32 | d, 8.2 | 7.05 |
| 33 | s | 2.20 |
| 34 | s | 3.95 |
| 35 | s | 3.67 |

TABLE 9

Antiinsectan Bioassay Results (100 ppm)

| Natural Product | RGR CEW | RFR NIT-A | RFR NIT-L |
|---|---|---|---|
| Carbonarin A | 0 | 31 | 0 |
| Carbonarin B | 6 | 33 | NTY |
| Carbonarin C | 0 | 7 | NTY |
| Carbonarin D | NTY | NTY | NTY |
| Carbonarin E | 26 | NTY | NTY |
| Carbonarin F | 0 | 7 | NTY |
| Carbonarin G | NTY | 33(105 ppm) | 31 |
| Carbonarin H | NTY | 20(45 ppm) | 19 |

RGR: % Reduction in Growth Rate. RFR: % Reduction in Feeding Rate. CEW (*Helicoverpa Zea*): Corn Earworm Larvae.
NIT-A (*Carpophilus hemipterus*): Driedfruit Beetle Adults. NIT-L (*Carpophilus hemipterus*): Driedfruit Beetle Larvae. NTY: Not Tested Yet.

TABLE 10

Fall Armyworm Leaf Disk Assays (50 μg/disk)

| Natural Product | Mortality | % Reduction in Damage Relative to Controls |
|---|---|---|
| Carbonarin B | 26 | 52 |
| Carbonarin C | 2 | 31 |
| Carbonarin F | 15 | 27 |
| Carbonarin G | NTY | 29 |
| Carbonarin H | NTY | 17 |

NTY: Not Tested Yet.

Literature Cited

Al-Musallam, A. Revision of the Black *Aspergillus* Species, Ph.D. Thesis, University of Utrecht, The Netherlands, 1980.

Bax, A. *J. Magn. Reson.* 1984, 57,314.

Bax, A.; Subromanian, S. *J. Magn. Reson.* 1986, 565.

Gloer, J. B.; TePaske, M. R.; Sima J.; Wicklow, D. T.; Dowd P. F. *J. Org. Chem.* 1988, 53, 5457.

Gloer, J. B.; Rinderknecht, B. L.; Wicklow, D. T.; Dowd, P. F. *J. Org. Chem.* 1989, 54, 2530.

Gorst-Allman, C. P.; Steyn, P. S.; Rabie, C. J. *J. Chem. Soc. Perkin Trans.* 1, 1980, 2474.

Priestap, A. H. *Tetrahedron* 1984, 40, 3617.

Priestap, A. H. *Magn. Reson. Chem.* 1986, 24, 875.

Summers, M. F.; Marzilli, L. G.; Bax, A. *J. Am. Chem. Soc.* 1986, 108, 4285.

Turner, W. B.; Aldridge, D. C. *Fungal Metabolites II*, Academic Press: New York, 1983, p. 21.

Wicklow, D. T.; Cole, R. J. *Can J. Bot.* 1982, 60, 525.

Wicklow, D. T.; Dowd, P. F.; TePaske, M. R.; Gloer, J. B. *Trans. Br. Mycol Soc.* 1988, 91, 433.

We claim:

1. A substantially pure carbonarin compound having the formula:

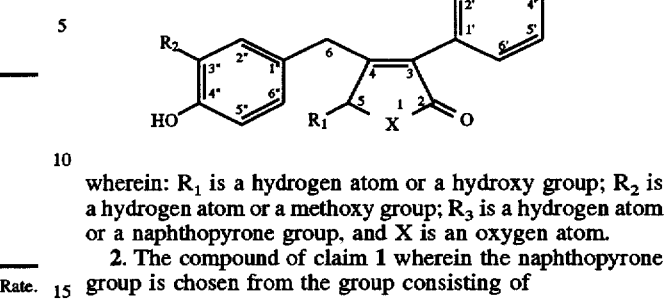

wherein: $R_1$ is a hydrogen atom or a hydroxy group; $R_2$ is a hydrogen atom or a methoxy group; $R_3$ is a hydrogen atom or a naphthopyrone group, and X is an oxygen atom.

2. The compound of claim 1 wherein the naphthopyrone group is chosen from the group consisting of

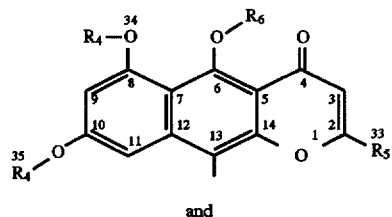

and

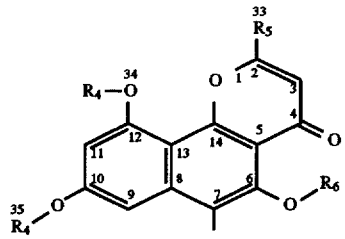

wherein $R_4$ and $R_5$ are individually a hydrogen or an alkyl group; and $R_6$ is —H or —C(=O)$R_7$ where $R_7$ is hydrogen or an alkyl group.

3. The compound of claim 2 wherein $R_6$ is —H or —C(=O)$R_7$ and $R_4$, $R_5$, $R_7$ are individually hydrogen or alkyl group chosen from the group consisting of methyl, ethyl, propyl, and butyl.

4. A composition for controlling insects comprising the substantially pure carbonarin compound of claim 1 and a carrier.

5. A composition for controlling insects comprising the substantially pure carbonarin compound of claim 2 and a carrier.

6. A composition for controlling insects comprising the substantially pure carbonarin compound of claim 3 and a carrier.

7. A substantially pure carbonarin compound having the formula:

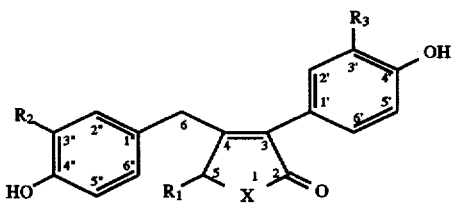

wherein: $R_1$ is a hydrogen atom or a hydroxy group; $R_2$ is a hydrogen atom or a methoxy group; $R_3$ is a hydrogen atom or a naphthopyrone group, and X is an NH group.

8. The compound of claim 7 wherein the naphthopyrone group is chosen from the group consisting of:

21

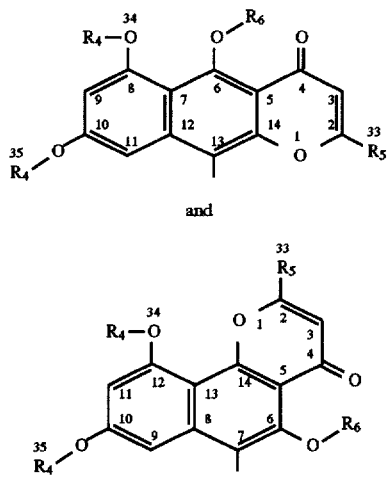

and wherein $R_4$ and $R_5$ are individually a hydrogen or an alkyl group; and $R_6$ is —H or —C(=O)$R_7$ where $R_7$ is hydrogen or an alkyl group.

9. The compound of claim 8 wherein $R_6$ is —H or —C(=O)and $R_7$ and $R_4$, $R_5$, $R_7$ are individually hydrogen or alkyl group chosen from the group consisting of methyl, ethyl, propyl, and butyl.

10. The compound of claim 9 wherein the naphthopyrone group is chosen from the group consisting of:

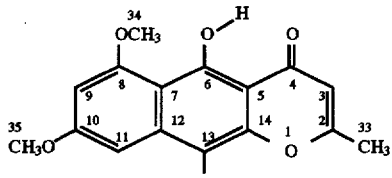

and

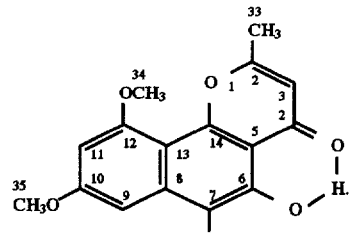

11. A composition for controlling insects comprising the substantially pure carbonarin compound of claim 7 and a carrier.

12. A composition for controlling insects comprising the substantially pure carbonarin compound of claim 8 and a carrier.

13. A composition for controlling insects comprising the substantially pure carbonarin compound of claim 9 and a carrier.

14. A composition for controlling insects comprising the substantially pure carbonarin compound of claim 10 and a carrier.

15. A substantially pure carbonarin selected from the group consisting of:

22

Carbonarin C:

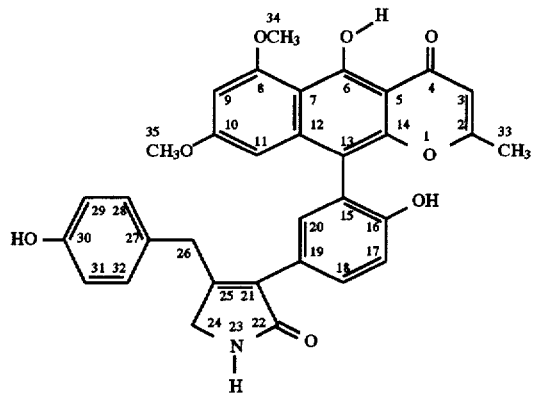

Carbonarin D:

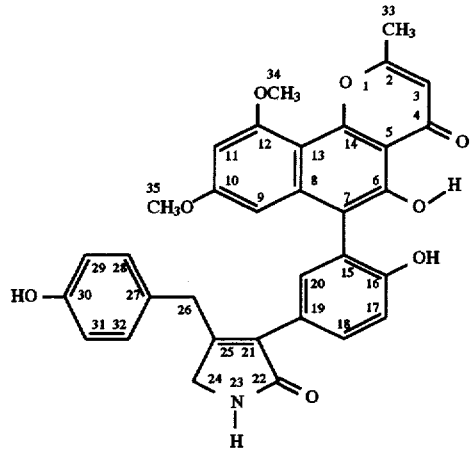

and Carbonarin E:

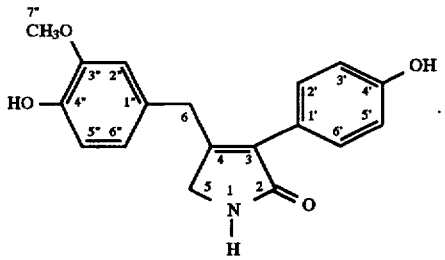

16. A composition for controlling insects comprising the substantially pure carbonarin of claim 15 and a carrier.

17. The composition of claim 16 including an amount of the carbonarin affecting insects of the Coleoptera species.

18. The composition of claim 16 including an amount of the carbonarin affecting insects of the Lepidoptera species.

19. The composition of claim 16 including an mount of the carbonarin affecting *Carpophilus hemipterus*.

20. The composition of claim 16 including an amount of the carbonarin affecting *Helicoverpa zea*.

21. The composition of claim 16 including an amount of the carbonarin affecting *Spodoptera frugiperda*.

22. A method of controlling insects comprising applying an effective amount of an insecticide selected from the group consisting of carbonarins C, D, and E.

23. The method of claim 22 wherein the insects are Coleoptera species.

24. The method of claim 22 wherein the insects are Lepidoptera species.

25. The method of claim 22 wherein the insects are *Carpophilus hemipterus*.

26. The method of claim 22 wherein the insects are *Helicoverpa zea*.

27. The method of claim 22 wherein the insects are *Spodoptera frugiperda*.

* * * * *

UNITED STATES PATENT AND TRADEMARK OFFICE
CERTIFICATE OF CORRECTION

PATENT NO.   :   5,672,621

DATED        :   September 30, 1997

INVENTOR(S)  :   Ali A. Alfatafta et al.

It is certified that error appears in the above-identified patent and that said Letters Patent is hereby corrected as shown below:

Column 21, line 25: "$R_6$ is -H or -C(=O) and $R_7$ and $R_4$, $R_5$, $R_7$"

should read: --$R_6$ is -H or -C(=O)$R_7$ and $R_4$, $R_5$, $R_7$--

Signed and Sealed this

Second Day of December, 1997

BRUCE LEHMAN

*Attest:*

*Attesting Officer*        *Commissioner of Patents and Trademarks*